United States Patent
Sethi

(10) Patent No.: US 9,220,413 B2
(45) Date of Patent: Dec. 29, 2015

(54) STENT APPARATUS WITH INTEGRATED IMAGING ELEMENT FOR IN SITU DETECTION OF BUILDUP OF MATERIAL IN A VASCULAR SYSTEM

(71) Applicant: Toshiba America Electronic Components, Inc., San Jose, CA (US)

(72) Inventor: Rakesh Sethi, San Jose, CA (US)

(73) Assignee: Toshiba America Electronic Components, Inc., Irvine, CA (US)

( * ) Notice: Subject to any disclaimer, the term of this patent is extended or adjusted under 35 U.S.C. 154(b) by 29 days.

(21) Appl. No.: 13/870,534

(22) Filed: Apr. 25, 2013

(65) Prior Publication Data

US 2014/0323875 A1 Oct. 30, 2014

(51) Int. Cl.
- *A61B 6/00* (2006.01)
- *A61B 5/00* (2006.01)
- *A61F 2/82* (2013.01)
- *A61B 5/02* (2006.01)

(52) U.S. Cl.
CPC ............... *A61B 5/0086* (2013.01); *A61B 5/004* (2013.01); *A61B 5/0044* (2013.01); *A61B 5/02007* (2013.01); *A61B 5/6862* (2013.01); *A61B 5/6876* (2013.01); *A61F 2/82* (2013.01)

(58) Field of Classification Search
None
See application file for complete search history.

(56) References Cited

U.S. PATENT DOCUMENTS

| | | | |
|---|---|---|---|
| 5,217,456 A | | 6/1993 | Narcisco, Jr. |
| 6,152,869 A | * | 11/2000 | Park et al. ........................ 600/3 |
| 6,442,413 B1 | * | 8/2002 | Silver ........................... 600/345 |
| 6,488,704 B1 | * | 12/2002 | Connelly et al. ............. 623/1.15 |
| 7,232,460 B2 | * | 6/2007 | Van Erlach et al. .......... 623/1.15 |
| 7,328,058 B2 | | 2/2008 | Iwanczyk et al. |
| 8,165,663 B2 | * | 4/2012 | Hyde et al. ..................... 600/476 |
| 8,512,219 B2 | * | 8/2013 | Ferren et al. ..................... 600/12 |
| 8,647,292 B2 | * | 2/2014 | Dacey et al. ..................... 604/8 |
| 2002/0128546 A1 | * | 9/2002 | Silver ........................... 600/365 |
| 2003/0100938 A1 | * | 5/2003 | Rubenchik et al. ............ 623/1.1 |
| 2004/0225326 A1 | * | 11/2004 | Weiner et al. ..................... 607/2 |
| 2004/0260391 A1 | * | 12/2004 | Santini et al. ............... 623/1.42 |

(Continued)

OTHER PUBLICATIONS

"Totally implantable real-time in vivo video telemenlry monitoring system for implant biocompatibility studies" Jun. 2001; R. D. Beach, Center for Biomater & Suyrgical Res.

(Continued)

*Primary Examiner* — James Kish
(74) *Attorney, Agent, or Firm* — Ulmer & Berne LLP

(57) ABSTRACT

According to one embodiment, an apparatus for detecting obstructions in biological vessels includes a cylindrical hollow stent with an expandable body portion having an outer surface configured to engage the inner surface of the lumen of the vessel to urge the vessel against collapse, and an imaging system operatively coupled with stent. The imaging system includes a first power source, a light generating element, a light sensor generating a first signal representative of light received by the sensor element from the light generating elements, and a processor unit receiving the first signal and processing the first signal in accordance with image processing logic stored in a memory of the processor unit to generate an image signal representative of as image of associated target material such as plaque obstructing the flow. The imaging system and stent may be formed on opposite sides of a flexible organic substrate.

17 Claims, 8 Drawing Sheets

(56) References Cited

U.S. PATENT DOCUMENTS

| | | | |
|---|---|---|---|
| 2005/0090761 A1* | 4/2005 | Carney | 600/549 |
| 2006/0074479 A1* | 4/2006 | Bailey et al. | 623/1.13 |
| 2010/0094138 A1 | 4/2010 | Gharib et al. | |
| 2012/0041534 A1 | 2/2012 | Clerc et al. | |

OTHER PUBLICATIONS

Worldwide Industrial Camera Directory: Vision Systems Design, Nov. 2007 "Linescan Camera Inspects Stent Surfaces" (www.vision-systems.com).

* cited by examiner

STENT APPARATUS WITH INTEGRATED IMAGING ELEMENT FOR IN SITU DETECTION OF BUILDUP OF MATERIAL IN A VASCULAR SYSTEM

FIELD

The subject application is directed generally to methods and apparatus for detection of material that may obstruct the flow of fluids through fluid conduits such as biological vessels. The application is particularly related to methods and apparatus providing in situ detection, visualization, and assessment of the buildup of plaque material in vascular systems of humans or animals.

BACKGROUND

Biological vessels of humans and animals carry fluids necessary to sustain life. Obstructions to the flow of fluids through these vessels can occur due to an accumulation of material caused by disease or other conditions. For example, plaque can form in cardiovascular systems because of heart disease, poor diet or heredity. Over time, the plaque can build up within the vessels supplying blood to the heart, for example, and block the flow of blood to the organ causing heart attacks or the like. The buildup of obstructive deposits in other vessels of the subject organism as well can lead to damage or failure of the corresponding organ dependent upon the biological fluid communicated by the vessel.

Plaque can be mechanically removed from vascular systems through various surgical procedures. However, this option is undesirable because it is expensive, highly invasive, and requires a long recovery time.

Angioplasty provides a non-surgical solution to the buildup of plaque in vascular systems. In this procedure, a catheter is introduced into the vascular system, usually through an artery such as the femoral artery. A small specialized deflated balloon is carried on the distal end of the catheter so that it may be positioned adjacent to the blockage area in accordance with corresponding guided movement of the catheter body. Once positioned, the balloon is temporally inflated causing the balloon to expand and the plaque accumulation to be compressed radially outwardly against the inner wall of the lumen of the target vessel. Thereafter, the catheter and balloon may be removed leaving an impression of the inflated balloon on the compressed plaque in the form of a smooth widened passage of the lumen of the vessel.

Proper routing of the balloon prior to inflation is important during angioplasty. For this, some catheters carry small cameras or other local visualization equipment to provide visual feedback to the interventionist of the position of the balloon relative to the target site. Post procedure visualization of the treatment area is not possible, however, because the cameras are removed from the patient together with retraction of the host catheter after the procedure.

Other methods used to insure positioning of the balloon relative to the plaque buildup during the procedure include concurrent imaging of the site using ultrasonic, CT, and/or MRI scanning technologies. However, MRI scanning is expensive and time consuming, and many patients prefer to avoid exposure to X-rays from CT procedures.

In some cases, mechanical devices such as stents have been placed at the target site directly after or during angioplasty for purposes of helping to prop open the target vessel. Typical stents are formed as a small expandable tube of shape retaining plastic material or an expandable shape retaining metal mesh. The stent is carried on the balloon area of the catheter and is thereby introduced into the target site during the angioplasty procedure at an operative position between the balloon and the inner wall of the lumen of the target vessel. Inflation of the balloon causes a coincident expansion of the stent. In the expanded conformation, the shape retaining stent is functional to hold the vessel open thereby enhancing the ability of the vessel to pass fluids therethrough well after the balloon is deflated and after the catheter is decoupled from the stent and withdrawn from the patient.

In addition to the post-procedure mechanical benefits afforded by stent devices, typical drug-eluting stents carry one or more medicaments for diffusion thereof over one or more predetermined time periods. One such medicament is aspirin and clopidogrel for reducing the risk of thrombosis leading to stent occlusion during the procedure or in the days following, or later.

Despite advances made in angioplasty procedures and in stent development, however, certain issues remain. Many patients experience a re-accumulation of plaque buildup. In some cases about 37% of the plaque returns in the patients' veins in the first 12 months after the procedure. A 10% buildup of plaque after the first month is not uncommon in some patients.

Unfortunately, inexpensive and non-invasive detection of post-procedure plaque re-accumulation is not available. Follow up CT scans expose the patients to undesirable X-rays and MRI sessions are time consuming and expensive. Post-angioplasty catheterization procedures are likewise time consuming but also introduce invasive equipment into the patients' body and, accordingly, carry some risks.

Methods and apparatus providing in situ detection, visualization, and assessment of the buildup of material such as plaque in vascular systems of humans and animals are therefore desirable.

DETAILED DESCRIPTION

Figure 1:
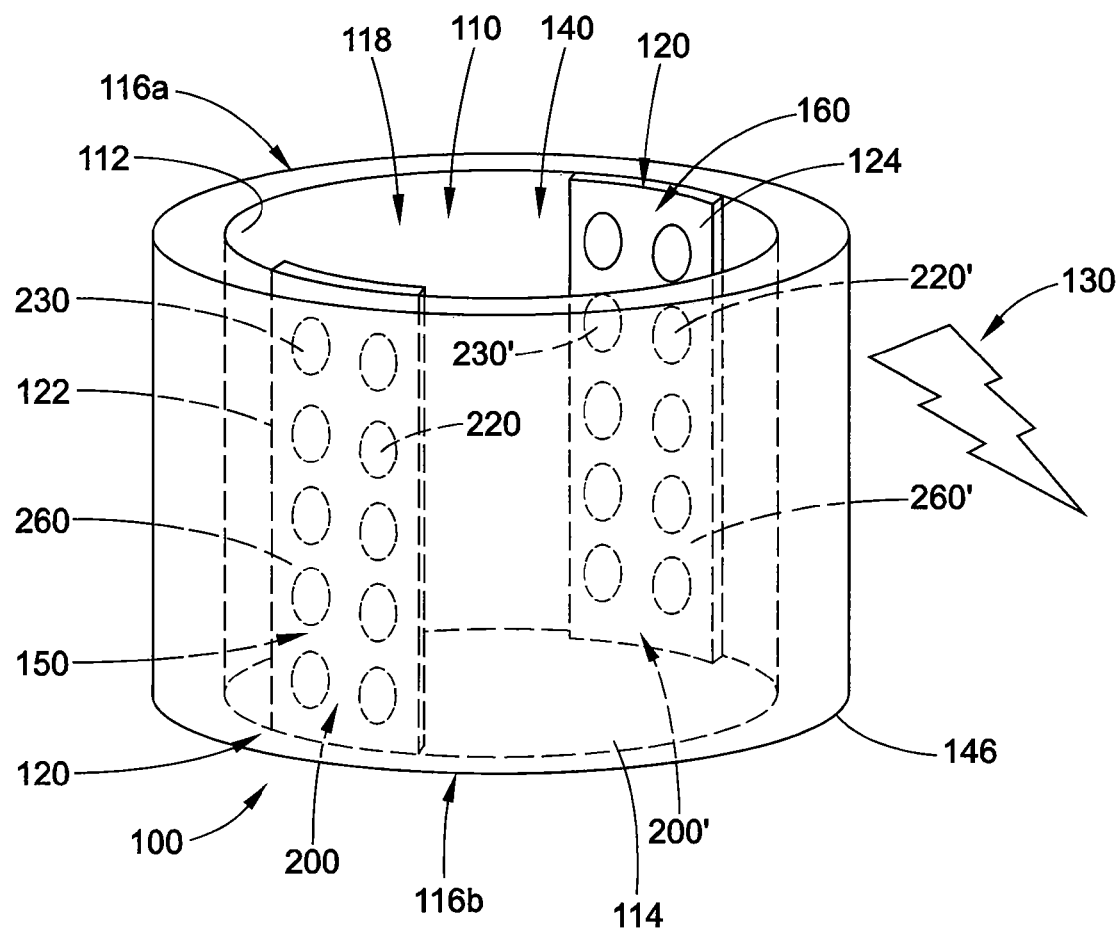
FIG. 1 is a schematic illustration of an apparatus for detecting, visualizing, and assessing obstructions in biological vessels in accordance with a first example embodiment.

In an embodiment, an apparatus for detecting an obstruction in a biological vessel includes a cylindrical hollow stent with an expandable body portion having an outer surface configured to engage the inner surface of the lumen of the associated biological vessel to urge the associated biological vessel against collapse, and an imaging system operatively coupled with stent. The imaging system includes a first power source, a light generating element, a light sensor generating a first signal representative of light received by the sensor element from the light generating elements, and a processor unit receiving the first signal and processing the first signal in accordance with image processing logic stored in a memory of the processor unit to generate an image signal representative of as image of associated target material such as plaque obstructing the flow. The imaging system and stent may be formed on opposite sides of a flexible organic substrate.

In accordance with an example embodiment, an apparatus is provided for detecting an obstruction in a biological vessel. The apparatus includes an elongate substantially cylindrical hollow first member, and an imaging system operatively coupled with the first member. The first member has an inner surface defining an opening through the first member, and an outer surface configured to engage an inner surface of a lumen of an associated biological vessel and further configured to locate the first member relative to the associated biological vessel to permit a flow of associated biological fluids in the associated vessel to pass through the opening. The imaging system of the example embodiment is configured to generate an image signal representative of an image of associated target material obstructing the flow of the biological fluid through the opening of the hollow first member.

In accordance with another embodiment, the elongate substantially cylindrical hollow first member is a stent including an expandable body portion having an outer surface configured to engage the inner surface of the lumen of the associated biological vessel to mechanically bias the associated vessel into an open position and against collapse.

In accordance with a further embodiment, the imaging system includes a first power source, a light generating element, a light sensor, and a processor unit. The light generating element is operatively coupled with the first power source and is configured to generate light. In one form, the light is visible light. However, the light may be ultraviolet light or infrared light. The light sensor is operatively coupled with the first power source and is configured to generate a first signal representative of light received by the light sensor element from the light generating element. The processor unit is operatively coupled with the power source, the light generating element, and the light sensor, and is configured to receive the first signal from the light sensor and to process the first signal in accordance with image processing logic stored in a memory of the processor unit to generate the image signal representative of the image of the associated target material obstructing the flow.

In accordance with another example embodiment, infrared light sources and light sensors are used, wherein the strength, timing, intensity or any combination of one or more of the strength, timing, and intensity of the infrared light penetrating the obstructive material in the vessel and falling onto the infrared sensors is detected. The infrared sensors are operable to convert the received infrared light signals to current and/or voltage signals representative of the opacity of the obstructive material or of other characteristics of the obstructive material. For certain materials such as plaque having a substantially constant density, the thickness of the buildup is determined in the example embodiment in accordance with a correlation between the determined opacity of the material and its density such as by use of a processing technique or algorithm executed by a processor of the system, by reference to a look up table stored in a non-transitory memory of the system, or the like.

In accordance with yet another example embodiment, paired sets of light sources and light sensors are operable within one or more preselected light bands for control by the system to provide a spectral imaging analysis of the obstructive material. In an example embodiment, a first paired set of light sources and light sensors are operable in the infrared range. Other sets of paired light sources and light sensors are operable in the near-infrared range, in the ultraviolet (UV) range, in the visible range, in combinations of one or more of these UV range, the visible range, IR range, or the near-IR range, or in any other range or ranges as necessary or desired.

In the example embodiment, spectral imaging is performed by repeatedly operating the light sources to generate light in multiple selected wavelengths within the selected light band range so that a set of data representative of a distribution of spectral information is obtained. The data provides a spectral map of the material and its distribution over time, and can be used to link the detection of the material and/or characteristics of the material with a set of one or more diseases or to its molecular structure.

With reference now to the drawings wherein the showings are for purposes of illustrating the example embodiments only, and not for purposes of limiting same, FIG. 1 is a schematic illustration of an apparatus 100 for detecting obstructions in biological vessels in accordance with a first embodiment. The apparatus 100 is functional as both a stent device for propping open a vessel, and also as an intelligent imaging system for viewing and assessing characteristics of obstructions within the vessel as will be described in detail below.

In general, the apparatus 100 includes an elongate substantially cylindrical hollow first member 110 and an imaging system 120 operatively coupled with the first member 110. The first member 110 has an inner surface 112 defining an opening 118 through the first member, and an outer surface 114 configured to engage an inner surface of a lumen of any associated biological vessel (not shown). The opening 118 extends between opposite first and second ends 116a, 116b of the first member 110. The outer surface 114 is further configured to locate the first member 110 relative to the associated biological vessel, such as by mutual mechanical contact therebetween for example, to permit a flow of associated biological fluids through the vessel to also pass between the first and second ends 116a, 116b and through the opening 118.

The imaging system 120 is operatively coupled with the first member 110 using a suitable adhesive such as by epoxies, cyanoacrylate adhesives (CAs) or the like or by any other one or more attachment techniques now known or hereinafter developed. In one embodiment the imaging system 120 and first member 110 are formed integrally using a flexible organic substrate and metal deposition techniques providing the imaging system directly onto the substrate as will be described in greater detail below. The imaging system 120 is configured to generate an electro-magnetic image signal 130 representative of an image of the volume within the opening 118 and including, if present, an image of an associated target material obstructing the flow through the opening 110. In the embodiment shown in FIG. 1, the imaging system 120 includes a first imaging system portion 122 and a second imaging system portion 124 disposed on opposite sides of the inner surface 112 of the first member 110. In the embodiment, components of the first imaging system portion 122 cooperatively interact with components of the second imaging system portion 124 in a manner to be described below in greater detail to develop the image signal 130 representative of one or more images of associated target material obstructing the flow within the opening 118. In an example embodiment, the first and second imaging system portions 122, 124 are identically formed.

In another embodiment, each of the first and second imaging system portions 122, 124 is autonomous and operates functionally independent of the other of imaging system portions, wherein a pair of image signals may be generated by the composite imaging system 120. In another embodiment, the first and second imaging portions cooperatively generate a single image signal 130.

It is to be appreciated that the first member 110 illustrated in the Figure is shown in a simplistic primitive form and, preferably, is a stent apparatus 140 comprising an expandable body portion 146 having an outer surface 144 configured to engage the inner surface of the lumen of the associated biological vessel, wherein the stent body portion mechanically holds the associated biological vessel against collapse. The stent 140 may be any commercially available stent now known or hereinafter developed.

In the embodiment, the first and second imaging system portions 122, 124 of the imaging system 120 are coupled with the stent 140 using any suitable adhesive such as by use of epoxies, cyanoacrylate adhesives or by other attachment techniques. However, in other embodiments described below, the expandable body portion 146 forming the stent 140 is integrally formed on portions of the imaging system 120 such as through use of metal deposition processes or the like.

Figure 2:
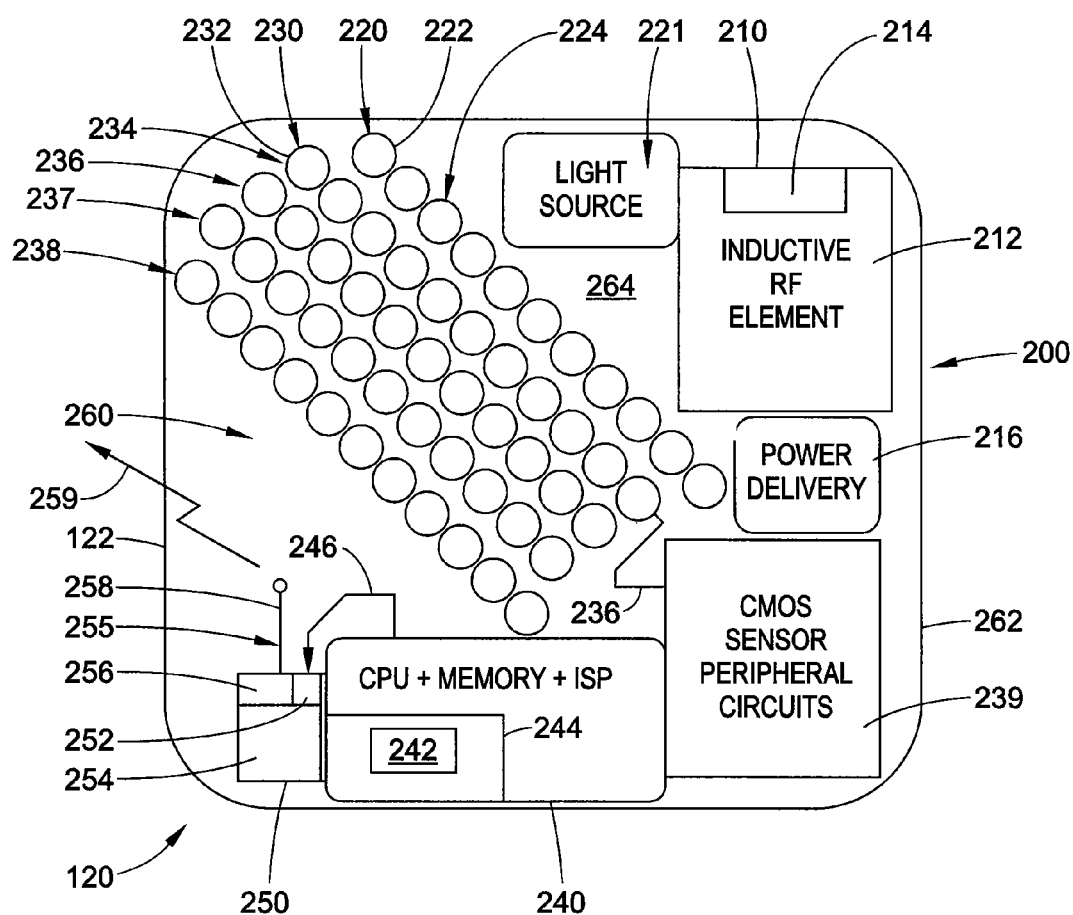
FIG. 2 is a block diagram of an imaging system used in any of the example embodiments of FIGS. 1 and 5-7.

FIG. 2 illustrates components of an example embodiment of the imaging system 120 removed from its operative coupled relationship with the stent 140 of FIG. 1. For ease of discussion, only an example embodiment of the first imaging system portion 122 is shown and described. The second imaging system portion 124 may be identical in form and function. With reference now to FIG. 2, the imaging system 120 of the example embodiment includes an imaging circuit 200 including a first power source 210, one or more light generating elements 220, 221 operatively coupled with the first power source 210, a light sensor 230 operatively coupled with the first power source 210, a processor unit 240 operatively coupled with the first power source 210, and a transmitter circuit 250 operatively coupled with the power source 210. Each of the components of the imaging circuit 200 are carried on a substrate member 260 at predetermined locations whereby interaction between the components of the imaging circuit can be effected.

In the example embodiment illustrated, the light generating element 220 includes one or more light sources 222 shown in the figure as a 1×11 array of light sources 224 configured to generate light. The light form may be of any type as necessary or desired including, for example, visible light, infrared light (IR), near infrared (near IR), ultra violet (UV) light, or any one or more combinations thereof. In one embodiment, the array of light sources 224 is an array of visible light emitting diodes (LEDs). In another embodiment the array of light sources 224 is an array of infrared (IR) light emitting diodes for emitting light in the infrared spectrum. The use of infrared light emitting light sources provides an enhanced dynamic range over visible light emitting sources for in situ vascular applications, particularly with regard to blood carrying vessels, whereby the use of light in the infrared spectrum generates beneficial high visibility images of the obstructive material such as plaque. In addition, the use of light in the infrared spectrum through infrared light emitting diodes and infrared light sensors enables an assessment of a thickness characteristics of the obstructive material such as plaque to be determined and communicated in the resultant image signal.

In another embodiment, the array of light sources 224 is an array of a mixture of visible light sources, infrared light sources, near infrared light sources, ultraviolet light (UV) sources, or any one or more combination of these. The light sources may be independently selectively operated by the processor unit 240 singularly or in groups to generate the light having desired characteristics in accordance with the end application of the apparatus or the like.

In one embodiment, the array of light sources 224 is an array of light sources operable in the visible light band. Also in this embodiment, each light generating element 220 of the 1×11 array of light sources 224 is configured to be operable by the processor 240 in one or more wavelengths within the visible light band range so that a set of data representative of a distribution of spectral information is obtained.

In another embodiment, the array of light sources 224 is an array of light sources operable in the IR light band. Also in this embodiment, each light generating element 220 of the 1×11 array of light sources 224 is configured to be operable by the processor 240 in one or more wavelengths within the IR light band range so that a set of data representative of a distribution of spectral information is obtained.

In a further embodiment, the array of light sources 224 is an array of light sources operable in the near-IR band. Also in this embodiment, each light generating element 220 of the 1×11 array of light sources 224 is configured to be operated by the processor 240 in one or more wavelengths within the near-IR light band range so that a set of data representative of a distribution of spectral information is obtained.

In a still further embodiment, the array of light sources 224 is an array of light sources operable in the UV light band. Also in this embodiment, each light generating element 220 of the 1×11 array of light sources 224 is configured to be operated by the processor 240 in one or more wavelengths within the UV light band range so that a set of date representative of a distribution of spectral information is obtained.

In yet a further embodiment, the light source 221 is operable by the processor 240 to generate light having varied wavelengths in one or more of the visible light band, the IR light band, the near-IR light band, and the UV light band, so that a set of data representative of a distribution of spectral information is obtained. This data provides a spectral map of the material and its distribution over time, and can be used to link the detection of the material and/or characteristics of the material with a set of one or more diseases to its molecular structure. Within each light band, the processor is configured to be stepped to sweep sub-wavelengths of light. For example, the system steps through each light wave length and develops an image. Each such stepping yields a slice of data including information comprising wave length and intensity that is related to a specific wave length of light. The steps are repeated wherein a distribution of spectral information of the target segment of the obstructive material such as plaque is built. The procedure provides a plaque spectral map and its buildup over time. This data is useful to link diseases and/or the molecular structure of the material as these characteristics have a degree of correlation.

The light sensor 230 of the exampled embodiment is a 1×11 array of sensors configured to generate a signal 236 representative of light received by the light sensor 230 from the light generating element 220 and/or from the corresponding light generating element 220' of the second imaging system portion 124. In an embodiment, sets of one or more of the light sensors are paired with sets of one or more of the light sources for communicating light signals therebetween in IR bands, near-IR bands, visible light bands, and UV bands.

In the example embodiment illustrated, the light sensor 230 includes one or more light sensor elements 232, wherein each of the light sensor elements is configured to generate a corresponding pixel signal representative of light received by the respective light sensor element. Further, in the illustrated embodiment, the light sensor 230 is in the form of an array of light sensor elements 234. Additional light generating and/or light sensing element 1×11 arrays 236, 237, 238 or of any size or location may be provided as well.

With continued reference to FIG. 2, the processor unit 240 is operatively coupled with the power source 210, the array of light sources 224, and the array of light sensor elements 234. The processor unit 240 is configured to receive the signal 236 representative of light received by the sensor 230 through one or move buffer circuits illustrated as CMOS sensor peripheral circuits 239 and to process the signal in accordance with image processing logic 242 stored in a non-transitory storage portion of the processor unit 240 such as an electronic memory 244 of the processor unit 240 to generate an output image signal 246 representative of the image of the volume within the opening 118 and including, if present, an image of the associated target material obstructing the flow through the opening 118 of the apparatus 100 (FIG. 1).

In the example embodiment, the transmitter circuit 250 is configured to receive the output image signal 246 from the processor unit 240 and convert it to the image signal 130 (FIG. 1) for transmission to an associated receiver unit (not shown) outside of the body of the patient.

The substrate member 260 has opposite first and second surfaces 262, 264, wherein the first surface 262 (back side as viewed in FIG. 2) is configured to engage the inner surface of the stent 140 and the second surface 264 (front side as viewed in FIG. 2) is configured to carry the light generating element 220 and the light sensor 230 in relative positions for communication of light from the light generating elements 220, 221 to the sensing element 230. In this way, a single large substrate 262 carrying a single imaging circuit 200 with a large light sensor array and large light generating array can be used in place of the pair of imaging system portions shown in FIG. 1. The orientation of the light sensor and light generating arrays relative to the edges of the substrate results in a spiral disposition of these elements as the substrate is bent or curled in embodiments using a flexible organic substrate. In that way, in these embodiments, light generated by the light generating elements is directed towards light sensors carried on a common flexible substrate shared with the light generating elements.

In the example embodiment, the transmitter circuit 250 is operatively coupled with the processor unit 240 and includes an input unit 252 configured to receive the output image signal 246 from the processor unit. A conversion unit 254 of the transmitter circuit 250 is operative to convert the output image signal 246 to a radio frequency signal 255 representative of the image signal 246. An output unit 256 of the transmitter circuit 250 is configured to output the radio frequency signal 255 to an operatively associated external receiver (not shown) outside of the patient's body. The transmitter circuit 250 may be any transmitter circuit now known or hereinafter developed capable of being positioned in situ within patient's body and broadcasting a signal to an associated receiver outside of the patient's body such as, for example, any wireless local area network (WLAN) device including those that are based on the Institute of Electrical and Electronic Engineering (IEEE) 802.15.6 wireless medical standard or any of the 802.11 standards commonly referred to as "WiFi" devices. Transmitter circuits using Bluetooth and/or Zigbee unlicensed technologies commonly used with cellular phones, handheld devices and personal computers can also be used in or as body-worn and/or implanted medical devices as described. These devices may operate in the 902-928 MHz, 2400-2483.5 MHz, and 5725-5850 MHz. bands at distances of up to a few hundred feet, or at any frequency range as necessary or desired. In an example embodiment, the transmitter circuit 250 is a circuit also authorized for marketing by the Food and Drug Administration (FDA) as a Class I, II or III medical device, for example. An antenna 258 is provided in the imaging circuit 200.

In the example embodiment, the antenna 258 is coupled with the output unit 256 of the transmitter circuit 250 and is operable to convert the radio frequency signal 255 to a wireless radio frequency signal 259 representative of the output image signal 246. In the example embodiment illustrated, the antenna 258 is formed integrally with the transmitter circuit 250. In other example embodiments, however, the expandable body portion 146 of the stent 140 is used as the antenna for converting the radio frequency signal to a wireless radio frequency signal representative of the image signal. In that embodiment, the antenna is formed integrally with the expandable body portion of the stent.

Still further in the example embodiment, the first power source 210 includes an inductive receiver unit 212, a power conversion unit 214, and an output unit 216. The inductive receiver unit 212 is configured to receive a wireless power signal from an operatively associated power generator (not shown) external to the patient's body. The power conversion unit 214 is configured to convert the wireless power signals to one or more wired power signals 218. The output unit 216 is operatively coupled with the light generating elements 220, 221, the light sensor 230, the processor unit 240, and the transmitter circuit 250 for delivering the one or more wired power signals 218 to the light generating element, the light sensor, the processor unit, and the transmitter unit.

Again, it is to be appreciated that the imaging circuit 200 illustrated in the Figure represents a first imaging system portion 122 of the imaging system 120 shown in FIG. 1. That is, the first and second imaging portions 122, 124 collectively form the overall imaging system 120 illustrated in FIG. 1 as a pair of spaced apart members. However, as shown, the collective substrate comprises a plurality of substrate portions 260, 260' arranged on the inner surface 142 of the stent 140 in a spaced apart relationship. As noted above, each of the first and second imaging system portions 122, 124 in the example embodiment comprise identically formed imaging circuits 200, 200' such as described above. Other forms of first and second imaging systems may be used as well such as, for example, a first imaging system portion having one or more light generating elements and the other imaging system portion having one or more light receiving elements wherein other portions of the imaging system may be carried on one or the other of the first or second imaging system portions, or carried remotely of the first and second imaging system portions while remaining operatively or functionally connected with the first and second imaging system portions.

In the example embodiment shown, only two imaging system portions 122, 124 are implemented, each having a substrate portion, but in other embodiments many imaging system portions may be provided wherein a first set 150 of the plurality of substrate portions carry at least one of the light generating elements 220, 221 and a second set 160 of the plurality of substrate portions carry at least one light sensing element 230. However, in embodiments having identically formed imaging circuits on opposite sides of the inner surface 142 of the stent member 140, each of the plurality of substrate portions 260, 260' carries at least one light generating element 220, 220' and/or 220, 221' and at least one light sensing element 230, 230'.

Figure 3A:
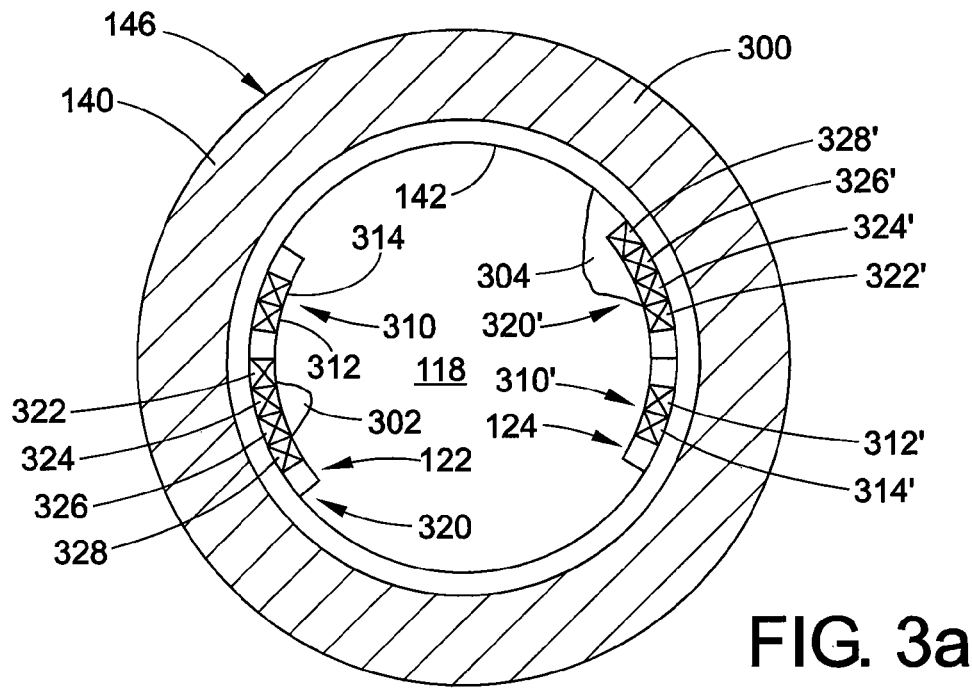
FIGS. 3a and 3b are cross-sectional views of the apparatus in FIGS. 1 and 2 during use in situ in a vessel of a biological host.
Figure 3B:
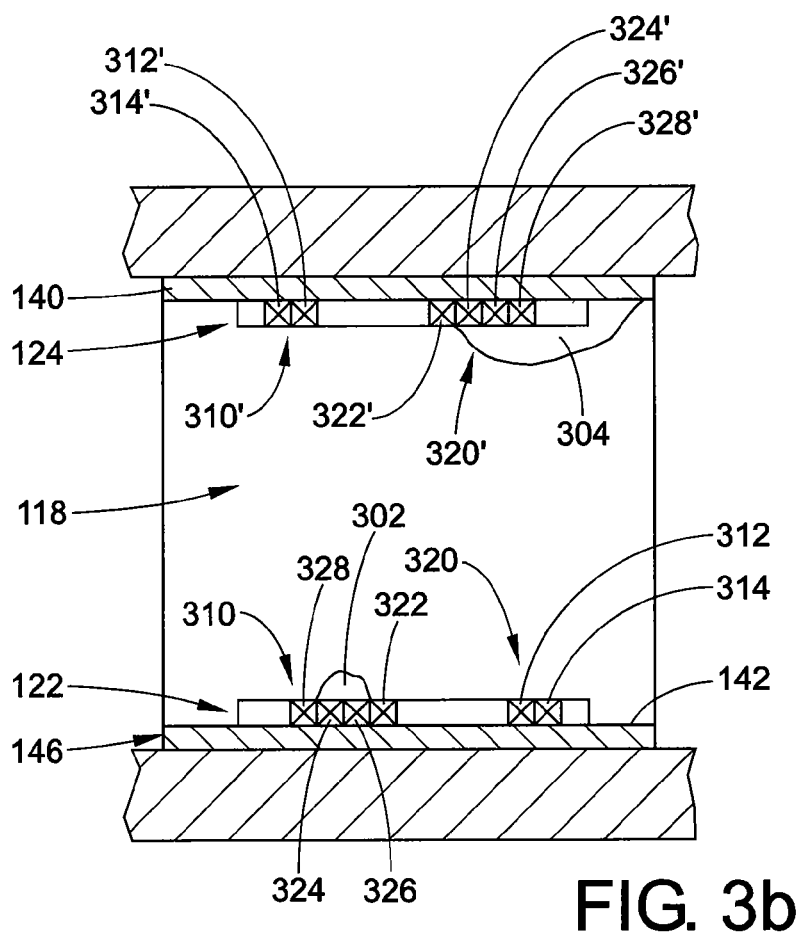

FIGS. 3a and 3b show, respectively, axially and longitudinal cross-sectional views of the apparatus 100 of FIGS. 1 and 2 disposed in situ within a vessel 300 of an associated organism. The expandable body portion 146 of the stent 140 is engaged with the inner surface of the vessel as illustrated. The inner surface 142 of the stent 140 carries the first and second imaging system portions 122, 124 on opposite sides of the vessel 300 as illustrated.

For purposes of describing operational features of the example embodiment, the vessel 300 is illustrated with first target material 302 formed on a first area of the first imaging system portion 122, and a second target material 304 formed on a second area of the second imaging system portion 124. The first and second target material 302, 304 may be, for example, plaque material obstructing the flow of blood or the like through the vessel 300.

For ease of discussion, the first imaging system portion 122 includes a first set 310 of light generating elements including an array of a pair of light sources 312, 314. In addition, the light sensor of the example embodiment illustrated includes a first set of light sensor elements 320 including an array of light sensor elements 322-328. In the illustrated embodiment, for purposes of discussion and illustration only, the first target material 302 is formed or was generated by the body of the patient in a manner to cover a pair of light sensor elements 324, 326.

In a similar fashion, for purposes of discussion and illustration only, the second target material 304 is formed on the second set of light sensor elements 320' covering light sensor elements 324', 326', and 328'.

As shown in the cross-sectional views of FIGS. 3a and 3b, the first set of light sensor elements 310 are operable to direct light onto the second set of light sensor elements 320'. Correspondingly, the second set of light generating elements 310' are operable to generate and direct light on to the first set of light sensing elements 320.

Figure 4A:
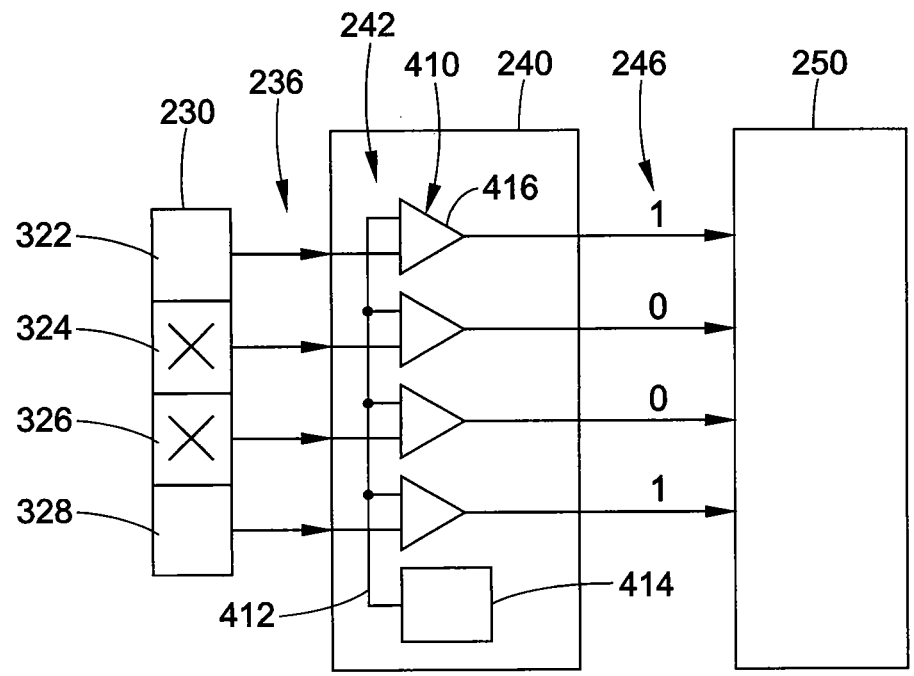
FIGS. 4a and 4b are functional schematics of imaging portions of the imaging system of FIGS. 1, 2, 3a, and 3b.
Figure 4B:
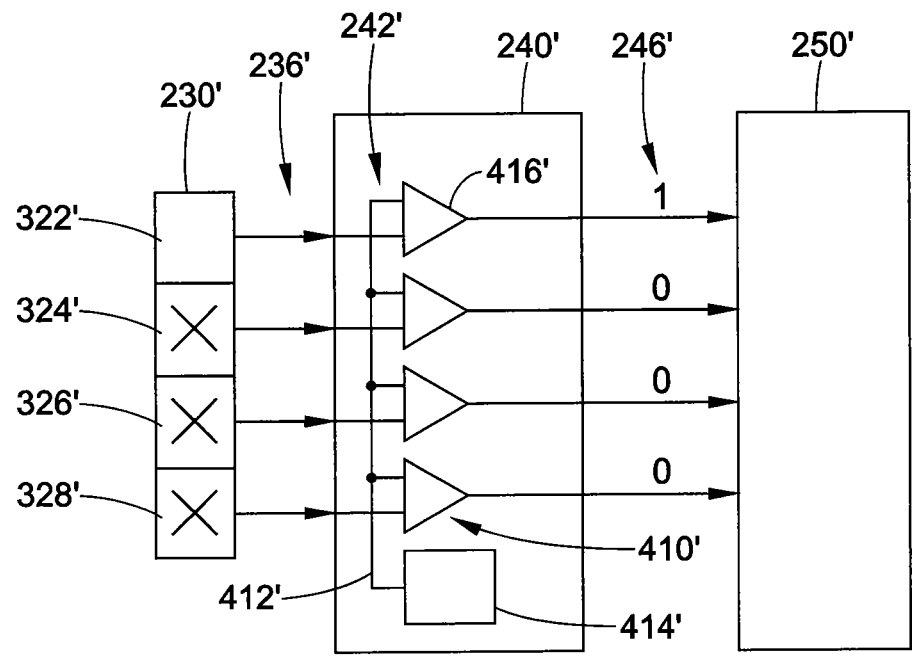

FIGS. 4a and 4b are schematic illustrations showing the processing performed by the processor units 240, 240' on each of the imaging systems 122, 124, respectively, for generating an intelligent image signal representative of one or more characteristics of the associated target material 302, 304 obstructing the flow to the vessel 300 (FIG. 3) such as for example size, location, and thickness characteristics. Each of the processor units 240, 240' includes respective processing logic 242, 242' for receiving the signals 236, 236' from the light sensors 230, 230' and converting the signals into an output image signal 246, 246' for use by the transmitter circuits 250, 250' in a manner substantially as described above. In the example embodiment shown the processing logic 242, 242' includes comparator logic 410, 410' for comparing the light sensor signals 236, 236' against predetermined threshold level signals 412, 412' representative of threshold data stored in a memory 414, 414' of the processor units. The processing logic 242, 242' is operable to compare the light sensor signal levels relative to the threshold levels using suitable comparison logic 416, 416'. The comparison logic is shown schematically as hardware comparison circuits but, in the example embodiment, may comprise hardware, software, or both software and hardware.

As shown in FIGS. 3a and 3b, the light sensor elements 324, 326 of the first set of light sensor elements 320 are blocked or occluded by the first target material 302. Accordingly, in one embodiment as shown in FIG. 4a, an assessment of the occluding material is performed wherein the light sensor elements 324, 326 generate a low level and, when compared against the threshold level 412, generate a logic level "0" as the output image signal 246. On the other hand, the light sensor elements 322, 328 are not occluded by the first target material 302 as shown in FIGS. 3a and 3b. Correspondingly, in the example embodiment, the comparison logic 416 generates an output signal 246 of a logic level "1" for these light sensing elements.

On the other side of the vessel, in the example illustrated, the second target material 304 blocks or otherwise occludes the light sensor elements 324', 326', and 328' of the second set of light sensor elements 320'. Accordingly, as shown schematically in FIG. 4b, the output image signal 246 comprises logic level "0" for each of the light sensor elements 324', 326', and 328' and a logic level "1" for the light sensor element 322'.

Although only a single 1×4 array is illustrated in the FIGS. 3a, 3b, 4a, and 4b, it is to be appreciated that the light sensor arrays can be formed of any size or dimension as necessary or desired. For example, the light sensor arrays may be configured as an array of 20×40, 200×400 or 2000×4000 light sensors, for example. As such, the logical states of individual sensor of the overall light sensor array produces an initial assessment of the obstructive material by developing information relating to the shape and location of the material wherein the shape and location of the material is essentially replicated or copied onto the overall light sensor array.

In addition, through the use of one or more infrared light generating elements and a corresponding one or more infrared light sensor arrays, a thickness characteristic of the obstructive material can be obtained as well in addition to the shape and location characteristic information. In this embodiment, the strength, timing, or intensity of the infrared light penetrating the obstructive material in the vessel and falling onto the infrared sensor array can be determined by the individual infrared light sensors and converted to variable current and/or voltage signals representative of the opacity and thus thickness of the material for materials such as plaque having a substantially constant density.

For infrared light sources and infrared light sensor arrays, the time of flight of pulsed light through occluded regions versus the time of flight of the light through non-occluded regions is measured and the difference is used to assess the thickness of the obstructive material in accordance with predetermined data representative of a likely density of the material. In FIGS. 3a, 3b, 4a, and 4b the light sensing elements 322, 328, and 322' would receive pulsed infrared light from light generators 310, 310' in advance of the light sensing elements 324, 326, 324', 326', and 328' due to the infrared light travel retardation through the obstructive material 302, 304. In this embodiment, the processor units 240, 240' include timing circuits and/or logic and timing comparison circuits and/or logic.

Figure 5:
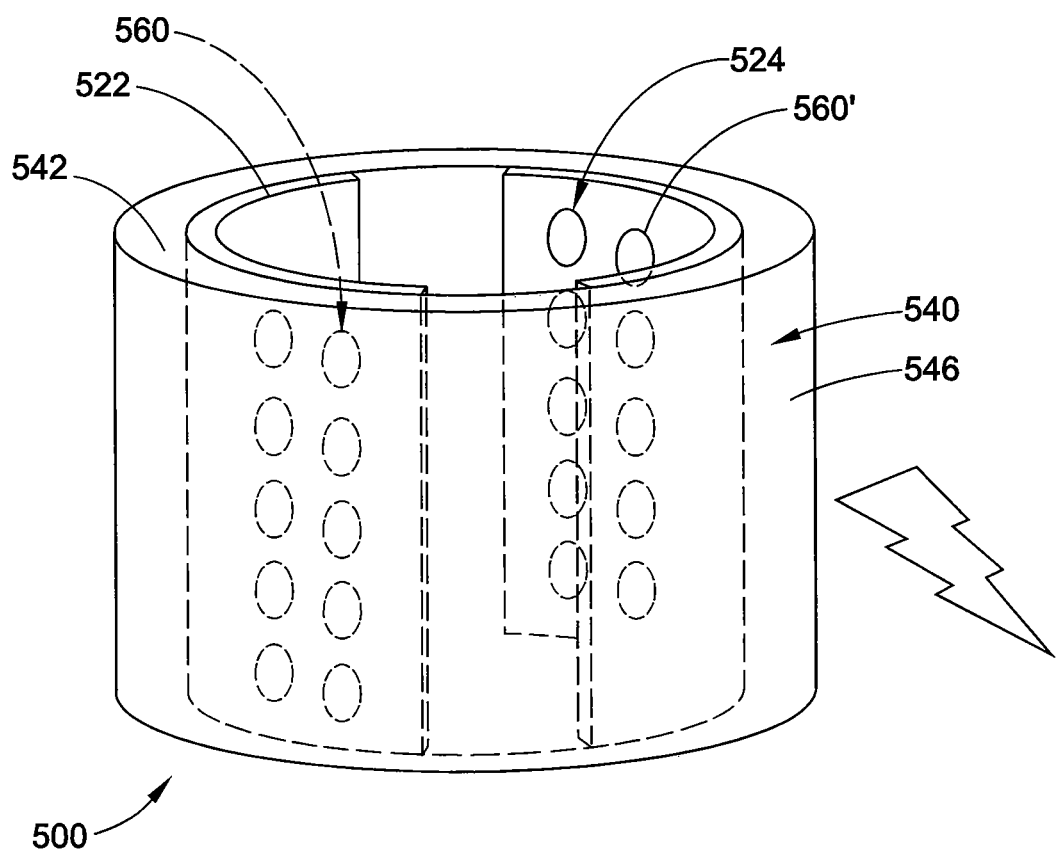
FIG. 5 is a schematic illustration of an apparatus for detecting obstructions in biological vessels in accordance with a second example embodiment.

FIG. 5 shows an example embodiment of an apparatus 500 for detecting an obstruction in a biological vessel wherein each of the first and second imaging system portions 522, 524 comprise substrate members 560, 560' comprising flexible silicon substrates. Accordingly, as shown, each of the first and second imaging system portions 522, 524 have a curved conformation corresponding with the inner surface 542 of the expandable body portion 546 of the stent 540.

Figure 6:
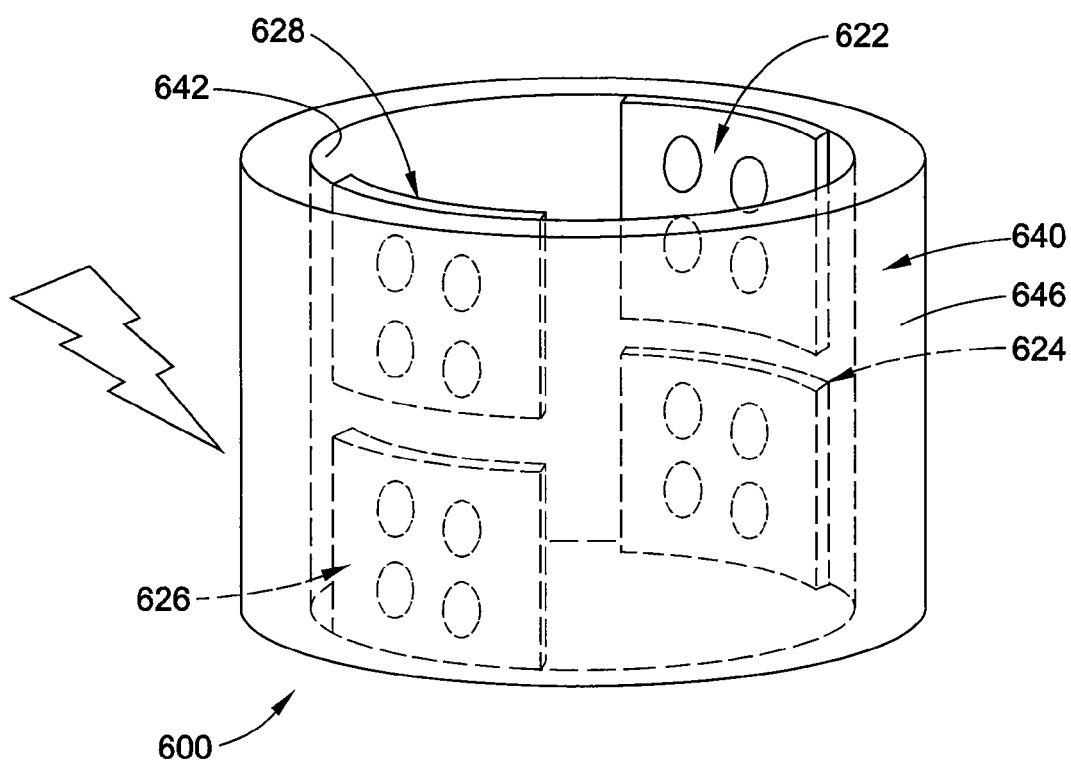
FIG. 6 is a schematic illustration of an apparatus for detecting obstructions in biological vessels in accordance with a third example embodiment.

FIG. 6 shows a further example embodiment of an apparatus 600 for detecting an obstruction in a biological vessel wherein the imaging system comprises plural imaging system portions 622-628 disposed in a spaced apart relationship relative to the inner surface 642 of the expandable body portion 646 of a stent 640. Each of the imaging system portions 622-628 includes flexible silicon or three-dimensional organic substrates 660, 660', 660", and 660'".

Figure 7:
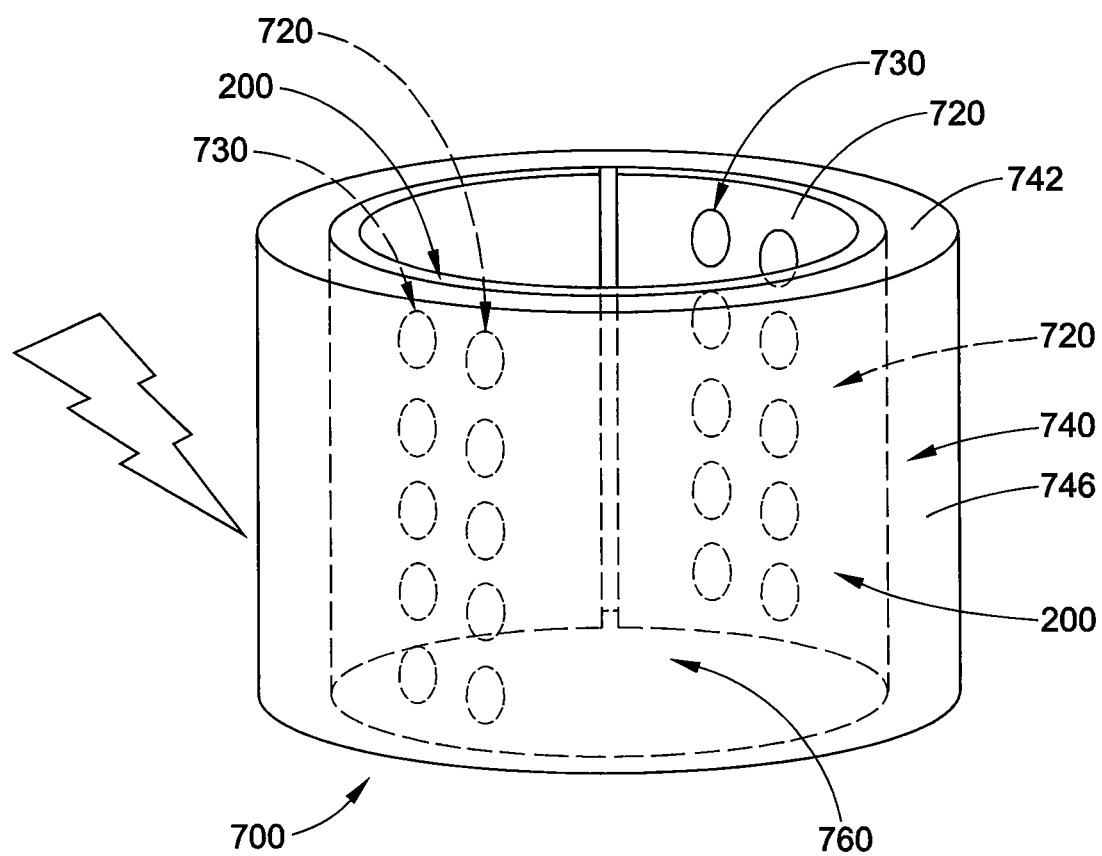
FIG. 7 is a schematic illustration of an apparatus for detecting obstructions in biological vessels in accordance with a fourth example embodiment; and, FIG. 8 is a flow chart for manufacturing and using an apparatus for detecting obstructions in biological vessels in accordance with an example embodiment.

FIG. 7 illustrates an apparatus 700 for detecting an obstruction in a biological vessel in accordance with a still further example embodiment. The imaging system 720 comprises a single flexible silicon or three-dimensional organic substrate member 760 carrying the imaging circuit 200 (FIG. 2) described above. As shown, sets of light generating elements 720 and sets of light sensor elements 730 are carried on opposite sides of the inner surface 742 of the expandable body portion 746 of a stent 740.

Figure 8:
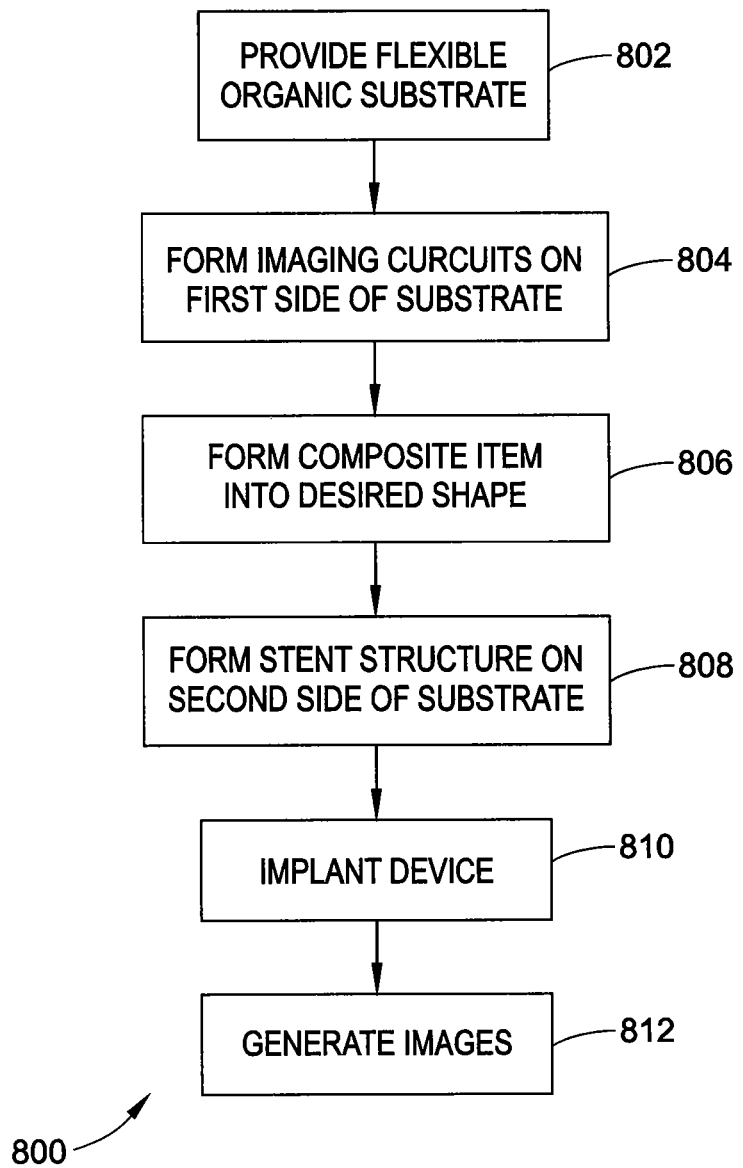

FIG. 8 is a flow chart of an example embodiment for fabricating an apparatus for detecting obstructions in biological vessels. The method 800 includes a first step 802 of providing a flexible organic substrate. The flexible organic substrate may be in the form of a three dimensional organic film or the like.

In step 804, one or more imaging circuits of the type described above, are formed or otherwise provided on a first side of the flexible organic substrate.

In step 806, the flexible organic substrate carrying the one or more imaging circuits is formed into a desired shape. For example, the flexible organic substrate may be formed into a hollow cylinder such as illustrated in FIGS. 1, and 5-7.

At step 808, a stent is formed on the second side of the organic substrate. In an example embodiment, the formation of the stent on the second side of the organic substrate may be my any means including, for example, by one or more metal deposition processes now known or hereinafter developed.

The composite structure is implanted at step 810 into a target organism such as, for example, into the vascular system of a human patient.

At step 812, images of the target tissue are generated by the implanted composite structure using methods, apparatus and techniques described above.

The embodiments herein have been described with reference to preferred structures and method steps. However, it is to be appreciated that the claims herein are not limited to those precise structures, steps, or their specific descriptions. Rather, the claims are to be given their broadest possible interpretation as appropriate.

In addition, while certain embodiments have been described, these embodiments have been presented by way of example only, and are not intended to limit the scope of the claimed inventions. Indeed, the novel embodiments described herein may be embodied in a variety of other forms; furthermore, various omissions, substitutions and changes in the form of the embodiments described herein may be made without departing from the spirit of the claimed inventions. The accompanying claims and their equivalents are intended to cover such forms or modifications as would fall within the scope and spirit of the inventions.

The invention claimed is:

1. An apparatus for detecting an obstruction in a biological vessel, the apparatus comprising:
   an elongate substantially cylindrical hollow first member having opposite first and second ends, an inner surface defining an opening between the first and second ends and through the first member, and an outer surface configured to engage an inner surface of a lumen of an associated biological vessel and locate the first member relative to the associated biological vessel to permit a flow of associated biological fluids in the associated vessel to pass between the first and second ends and through the opening, the substantially cylindrical hollow first member further having a stent, the stent comprising an expandable body portion the outer surface configured to engage the inner surface of the lumen of the associated biological vessel to deter collapse; and;
   a light source operatively coupled to receive power from an associated power source, the light source operable to generate light having multiple wavelengths;
   an imaging system operatively coupled with the first member, the imaging system being configured with a two dimensional array of adjacent light sensors operable to generate pixel signals representative of a two dimensional image of a shape and location of associated target material obstructing the flow in accordance with illumination of the target material by the light source such that each light sensor generates its associated pixel signal in response to multiple wavelengths;
   a CMOS sensor buffer circuit configured to buffer the pixel signals; and
   the imaging system further configured with an image processor having a memory, associated with the array of light sensors, the image processor operable to receive an output from the CMOS sensor buffer circuit, the image processor further operable to store data corresponding to generation of the image;
   a conversion unit operable to convert the data corresponding to generation of the image to a radio signal output, and
   an antenna formed integrally with the expandable body portion of the stent such that the expandable body portion of the stent is used as an antenna for converting the radio signal to a wireless radio signal.

2. The apparatus according to claim 1, wherein:
   the imaging system is operatively coupled with the stent and comprises:
   a first power source;
   a light generating element operatively coupled with the first power source, the light generating element generating light;
   the light sensor array operatively coupled with the first power source, the light sensor array generating a first signal representative of light received by the light sensor array from the light generating element; and,
   a processor unit operatively coupled with the first power source, the light generating element, and the light sensor array, the processor unit comprising a non-transitory storage and an input for receiving the first signal and processing the first signal in accordance with image processing logic stored in the non-transitory storage of the processor unit to generate the image data.

3. The apparatus according to claim 2, further comprising:
   a substrate having opposite first and second surfaces, wherein the first surface of the substrate is configured to engage the inner surface of the stent and the second surface of the substrate is configured to carry the light generating element and the sensing array in relative positions for communication of the light between the light generating element and the sensing array.

4. The apparatus according to claim 3, wherein:
   the light sensor array comprises a plurality of light sensing elements of the array arranged on the substrate and generating a plurality of pixel signals, wherein each of the plurality of light sensing elements is configured to generate a corresponding pixel signal having a level representative of light received by a respective sensing element from the light generating element; and,
   the processor unit is configured to receive and process the plurality of pixel signals in accordance with the image processing logic stored in the non-transitory storage of the processor unit to generate the image data, wherein the level of each pixel signal is representative of a characteristic of the associated target material.

5. The apparatus according to claim 4, wherein:
a light generating array including the light generating element configured to generate infrared light;
the light sensor array comprises the plurality light sensing elements comprised of infrared light sensing elements configured to receive the infrared light and generate a plurality of pixel signals, wherein each of the plurality of the infrared light sensing elements is configured to generate a corresponding pixel signal having a level representative of a level of infrared light received by a respective infrared light sensing element from the light generating array; and,
the processor is configured to receive and process the plurality of pixel signals in accordance with the image processing logic stored in the non-transitory storage of the processor unit to generate an assessment image data, wherein the level of each pixel signal is representative of a thickness characteristic of the associated target material obstructing the flow of the biological fluid in the associated vessel.

6. The apparatus according to claim 4, further comprising:
a transmitter unit operatively coupled with the processor and the antenna, the transmitter unit comprising an input unit receiving the image signal, the conversion unit configured to convert the image signal to the radio signal, and an output unit configured to output the radio signal to an operatively associated external receiver.

7. The apparatus according to claim 4, wherein:
the first power source comprises an inductive receiver unit configured to receive a wireless power signal from an operatively associated external power generator, a power conversion unit configured to convert the wireless power signal to one or more wired power signals, and an output unit operatively coupled with the light generating element, the light sensor array, the processor unit, and the transmitter unit for delivering the one or more wired power signals to the light generating element, the light sensor array, the processor unit, and the transmitter unit.

8. The apparatus according to claim 3, wherein:
the substrate comprises a plurality of substrate portions arranged on the inner surface of the stent in a spaced apart relationship.

9. The apparatus according to claim 8, wherein:
a first set of the plurality of substrate portions carry at least one light generating element; and,
a second set of the plurality of substrate portions carry at least one light sensing element.

10. The apparatus according to claim 8, wherein:
each of the plurality of substrate portions carries at least one light generating element and at least one light sensing element.

11. The apparatus according to claim 3, wherein:
the substrate comprises a flexible substrate member disposed in a rolled configuration substantially defining a hollow cylindrical substrate;
the light generating element comprises a plurality of light generating members;
the light sensor array comprises a plurality of light sensor members; and,
one or more of the plurality of light generating members are operatively paired with one or more of the plurality of light sensor members.

12. The apparatus according to claim 3, wherein:
the substrate comprises a flexible substrate member disposed in a rolled configuration substantially defining a hollow cylindrical substrate;
the light generating element comprises a plurality of infrared light generating members generating infrared light;
the light sensor array comprises a plurality of infrared light sensor members configured to receive the infrared light; and,
one or more of the plurality of infrared light generating members and one or more of the plurality of infrared light sensor members are disposed on relative opposite sides of a lumen defined by the hollow cylindrical substrate.

13. The apparatus of claim 3, wherein:
the substrate comprises a flexible substrate member disposed in a rolled configuration substantially defining a hollow cylindrical substrate;
the light generating element comprises a plurality of light generating members;
the light sensor array comprises a plurality of light sensor members; and
one or more of the plurality of light generating members are operatively paired with one or more of the plurality of light sensor members such that the wavelength of the emitted light is varied allowing the capture of spectral imaging of plaque by correlated light data by the light sensors of the array.

14. A method for detecting material in an associated conduit communicating a fluid, the method comprising;
engaging an inner surface of the associated conduit with a stent member;
generating light having multiple wavelengths by a light generating element carried on the stent member adjacent a first side of the associated conduit;
receiving the light by a two dimensional array of adjacent light sensor elements carried on the stent member adjacent a second side of the associated conduit opposite the first side, wherein the light received by each light sensor element includes light having multiple wavelengths which is passed through the fluid communicated by the associated conduit;
generating, by the light sensor element array, pixel signals representative of a two dimensional image of a shape and location of obstructive material from light received by the light sensor array from the light generating element;
buffering image data corresponding to the pixel signals in a CMOS sensor buffer circuit;
converting the data to a radio signal output; and
wirelessly transmitting by an antenna formed integrally with the stent member disposed in situ within the associated conduit an obstructive material the image data to an associated receiver disposed outside of the associated conduit, the obstructive material signal being representative of data corresponding to the image received by the light sensor array.

15. The method according to claim 14 wherein:
the generating light comprises generating infrared light; and
the generating the image data comprises generating the image data representative of a thickness of the obstructive material in accordance with a characteristic of the infrared light received by the light sensor array from the light generating element.

16. The method according to claim 14 wherein;
the generating light comprises generating a plurality of light beams, each of the plurality of light beams having a different wavelength within a preselected light wavelength band; and
the transmitting the obstructive material signal comprises transmitting a spectral imaging signal representative of at least one characteristic of the material in the associated conduit.

17. The method according to claim 16 wherein:
the generating the plurality of light beams comprises generating a plurality of light beams having different wavelengths within at least one or more of a visible light band, an infrared light band, a near-infrared light band, and an ultra violet light band.

* * * * *